(12) United States Patent
Mayer

(10) Patent No.: US 10,525,003 B2
(45) Date of Patent: Jan. 7, 2020

(54) ANTIFUNGAL COMPOSITION

(75) Inventor: Friedrich Karl Mayer, Oberwil (CH)

(73) Assignee: GSK CONSUMER HEALTHCARE S.A., Prangins (CH)

( * ) Notice: Subject to any disclaimer, the term of this patent is extended or adjusted under 35 U.S.C. 154(b) by 1215 days.

(21) Appl. No.: 11/992,823

(22) PCT Filed: Sep. 27, 2006

(86) PCT No.: PCT/EP2006/066816
§ 371 (c)(1),
(2), (4) Date: Mar. 26, 2008

(87) PCT Pub. No.: WO2007/039533
PCT Pub. Date: Apr. 12, 2007

(65) Prior Publication Data
US 2009/0088434 A1    Apr. 2, 2009

Related U.S. Application Data

(60) Provisional application No. 60/723,163, filed on Oct. 3, 2005, provisional application No. 60/722,625, filed on Sep. 29, 2005.

(51) Int. Cl.

| | | |
|---|---|---|
| *A61K 9/06* | (2006.01) |
| *A61K 31/137* | (2006.01) |
| *A61K 31/5375* | (2006.01) |
| *A61K 47/32* | (2006.01) |
| *A61K 47/38* | (2006.01) |
| *A61K 9/00* | (2006.01) |
| *A61K 9/70* | (2006.01) |

(52) U.S. Cl.
CPC ............. *A61K 9/0014* (2013.01); *A61K 9/06* (2013.01); *A61K 9/7015* (2013.01); *A61K 31/137* (2013.01); *A61K 31/5375* (2013.01); *A61K 47/32* (2013.01); *A61K 47/38* (2013.01)

(58) Field of Classification Search
CPC .................................................. A61K 31/4192
USPC ...................................................... 514/239.5
See application file for complete search history.

(56) References Cited

U.S. PATENT DOCUMENTS

| | | | |
|---|---|---|---|
| 5,006,346 A * | 4/1991 | Edgren et al. ................. | 424/473 |
| 5,519,059 A * | 5/1996 | Sawaya .......................... | 514/599 |
| 5,681,849 A | 10/1997 | Richter et al. | |
| 5,856,355 A | 1/1999 | Richter et al. | |
| 5,866,105 A | 2/1999 | Richter | |
| 6,005,001 A | 12/1999 | Richter et al. | |
| 6,060,547 A * | 5/2000 | Canter et al. ................. | 524/280 |
| 6,121,314 A | 9/2000 | Richter et al. | |
| 6,143,794 A * | 11/2000 | Chaudhuri et al. ........... | 514/655 |
| 6,214,360 B1 | 4/2001 | Richter et al. | |
| 6,241,360 B1 | 4/2001 | Richter | |
| 6,224,887 B1 | 5/2001 | Samour et al. | |
| 6,319,509 B1 | 11/2001 | Richter | |
| 6,005,001 C1 | 6/2008 | Richter et al. | |
| 6,121,314 C1 | 4/2009 | Richter et al. | |
| 2005/0175641 A1 | 8/2005 | Deo | |

FOREIGN PATENT DOCUMENTS

| | | |
|---|---|---|
| CA | 1175355 | 10/1984 |
| EP | 0 319 965 | 6/1989 |
| EP | 0 515 312 | 11/1992 |
| EP | 0 515 310 | 6/2002 |
| EP | 1 627 610 | 2/2006 |
| RU | 2 110 257 | 5/1998 |
| WO | WO 9823291 | 4/1998 |
| WO | WO 2005013955 | 2/2005 |

OTHER PUBLICATIONS

RU 2 110 257 Non Patent Publication—English Language Abstract.
Ortonne, J. P., et al., Efficacy and safety of a new single-dose terbinafine 1% formulation in patients with tinea pedis (athlete's foot): A randomized double-blind.
3rd Party Observations Jan. 11, 2011 concerning EPA 06793874.6.
Ortonne, J.P., et al., Efficacy and safety of a new single-dose terbinafine 1% formulation in patients with tinea pedis (athlete's foot), Journal of the European Academy of Dermatology and Venereology 2000 United Kingdom, vol. 20, No. 10, 2000, pp. 1307-1313.
AN-2003: 1006816 (Abstract of WO 03/105903, Pola Chem Ind Inc.).
Masayuki, et al., JP2002068974, Antifungal Medicine Composition, English Translation of Abstract.
Akira, et al., JP2002068975, Antifungal Medicine Composition, English Translation of Abstract.

* cited by examiner

*Primary Examiner* — Yong S. Chong
(74) *Attorney, Agent, or Firm* — Diane E. Furman; Joshua C. Sanders

(57) ABSTRACT

The invention provides a topical liquid antifungal composition containing an antifungal agent, a film-forming agent and a solvent. The composition is applied on the infected skin area to form a film that delivers the active agent. The invention also provides a method for treating a fungal infection on the skin by applying the topical antifungal composition that forms a film on the skin.

24 Claims, No Drawings

ANTIFUNGAL COMPOSITION

The invention relates to a topical pharmaceutical composition with anti-fungal activities and to a method for treating fungal infections.

Dermatophytes are fungi that can cause infections of the skin. The organisms colonize the keratin tissues and cause fungal infections. The symptoms of dermatophyte infections, such as athlete's foot, are characterized by lesions between the toes, with possible extension to the lateral surfaces and soles. Redness, itching and scaling are the most common signs and symptoms of the infected area, and the infection is contagious and may be recurrent. The organisms are transmitted by either direct contact with infected host (human or animal) or by direct or indirect contact with, for example, infected exfoliated skin or hair in combs, hair brushes, clothing, furniture, towels and locker room floors. There is an increased susceptibility to infection when there is a pre-existing injury to the skin such as scares, burns, marching, excessive temperature and humidity.

There are topical pharmaceutical compositions that are designed to treat dermatophyte infections. These topical compositions are commercially available, for example, in cream, ointment, powder, solution and spray forms, and they are applied once or twice daily for one week to four weeks or more to treat the infection. Since these compositions require a treatment regimen over one to several weeks, fully complying with the regimen to a successful treatment is difficult and premature terminations of the treatment are common.

Another form of delivering pharmaceutically active agent is a film-forming liquid composition. Liquid wart remover compositions and nail varnish compositions to treat onychomycosis are examples such compositions. These compositions are applied on the effected area repeatedly to treat the problem. For example, such onychomycosis treatment composition must be applied on the infected area and then removed before the composition can be applied again. The application and removal procedures are repeated periodically over an extended period of time to treat onychomycosis. Although these film-forming compositions may not be required to be applied on a daily basis, the application regimen is not simple to comply with.

It is highly desirable to have an antifungal composition that is highly efficacious and has a simple application regimen that can be easily complied with.

SUMMARY OF INVENTION

The present invention provides a topical liquid antifungal composition containing an antifungal agent, a film-forming agent and a solvent. The composition is applied on the infected skin to form a film and has a mycological cure rate of at least 50% with one application to the infected area. The invention also provides a method for treating a fungal infection on the skin by applying the topical antifungal composition that forms a film on the skin and allowing the film to stay on the skin for at least 48 hours. More specifically, the invention provides a method for treating a fungal infection of the skin, which has the step of topically applying a film-forming composition to form a film on the infected area of the skin. The composition contains an antifungal agent selected from imidazole, triazole, or allyalimine, a film-forming polymer selected from the group consisting of acrylate polymers, acrylate copolymers, alkyl olefinic acid, alkyl olefinic acid ester copolymers, amide/olefinic acid, amide/olefinic acid copolymers, polyvinyl acetate, polyvinylpyrrolidone, vinylpyrrolidone-vinylacetate copolymer, hydroxyalkyl cellulose, and alkyl cellulose, and a solvent selected from ethanol, isopropanol, acetone, ethyl acetate, and a mixture of water and one or more of the solvents.

The composition of the present invention is highly efficacious and typically requires only one application to treat a fungal infection on the skin, such as tinea pedis, tinea corporis, tinea cruris, and tinea capitis. Although the composition is efficacious with only one application, it can applied more than one time to the infected area of the skin. The term skin as used herein indicates the outer surface of the body other than the nail and cornea. The term mycological cure rate as used herein indicates the percentage of specimens which have no visual evidence of mycology examined under a microscope.

DETAILED DESCRIPTION OF THE INVENTION

The invention provides a single-dose application composition for treating dermyotophyte infections, making the treatment simple. In addition, the composition is highly efficacious in curing or treating fungal infections on the skin. The convenient single-dose regimen and the high efficacy of the composition make treatment of the infectious disease simple to comply with. The composition, which contains a film-forming agent, an antifungal agent and a solvent, is formulated to adhere to and stay on the skin for at least 48 hours, preferably at least 60 hours, more preferably at least 72 hours, although minor portions of the film can be removed or abraded away during that time. It has been found that one application of the composition of the invention provides a treatment efficacy that is equivalent to or better than the treatment result of strictly following the repeated application regimens of currently available over-the-counter antifungal pharmaceutical products for a period of one to four weeks.

Antifungal agents suitable for the invention include imidazloes, traizoles, allylamines, and mixtures thereof. Suitable imidazloes include miconazole, ketoconazole, clotrimazole, econazole, mebendazole, bifonazole, butoconazole, fenticonazole, isoconazole, oxiconazole, sertaconazole, sulconazole, thiabendazole, and tiaconazole. Preferred are miconzalo, ketoconazole and clotrimazole, and more preferred is clotrimazole. Suitable triazoles include fluconazole, itraconazole, ravuconazole, and posaconazole. Suitable allylamines include terbinafine, amorolfine, naftifine, and butenafine. Of these, preferred are terbiafine and butenafine, and more preferred are terbinafine. All of the antigungal agents can be in a pharmaceutically active salt form. Examples of suitable salt forms are the hydrochloride, lactate and ascorbate forms. Particularly preferred antifungal agents are allylamines and salts thereof, and more particularly preferred are terbinafine and terbinafine hydrochloride. The composition contains between 0.5% w/w and 30% w/w of an antifungal agent, preferably between 0.75% w/w and 20% w/w, more preferably between 0.9% w/w and 15% w/w, most preferably between 1% w/w and 10% w/w. One particularly desirable embodiment of the invention contains between 0.9% w/w and 1.2% w/w, preferably between 0.95% w/w and 1.15% w/w, more preferably 0.97% w/w and 1.125% w/w, and most preferably 1% w/w, of terbinafine.

Film-forming agents suitable for the invention include hydrophilic and hydrophobic film-forming polymers that form a film when applied on the skin. The composition contains a sufficient amount of a film-forming polymer to form a layer of film when applied on the skin, and it can contain up to 50% w/w of a film-forming polymer. Desirably, the film-forming polymers form a film on the skin, which sturdily adheres to the skin, such that the film stays on the skin for a required period of time even when exposed to typical hygienic cleaning cycles. In general, the film-forming agent is applied with a solvent on the skin, and when the solvent is evaporated, the agent forms a film on the skin. Suitable hydrophobic polymers include acrylate polymers, acrylate copolymers, alkyl olefinic acid, alkyl olefinic acid ester copolymers, amide/olefinic acid, amide/olefinic acid copolymers, and polyvinyl acetate. Preferred hydrophobic polymers include octylacrylamide, octylacrylamide acrylate copolymer, octylpropenamide acrylate copolymer, aminoalkyl methacrylate copolymer, ammonio methacrylate copolymer, polyvinylacetate, and alkyl acrylate methylmethacrylate copolymer. Suitable hydrophilic polymers include polyvinylpyrrolidone, vinylpyrrolidone-vinylacetate copolymer, hydroxyalkyl cellulose, and alkyl cellulose. Preferred hydrophilic polymers include hydroxypropyl cellulose, hydroxypropylmethyl cellulose, and polyvinylpyrrolidone. It is desirable to have both hydrophilic and hydrophobic polymers in the composition. As a preferred embodiment, the hydrophilic polymer is present in an amount between 0.05% w/w and 30% w/w of the composition, preferably between 0.5% w/w and 10% w/w, and more preferably 1% w/w and 5% w/w, and the hydrophobic polymer is present in an amount between 0.05% w/w and 30% w/w of the composition, preferably between 1% w/w and 10% w/w, and more preferably between 3% w/w and 7% w/w. An exemplary desirable composition has between 4% w/w and 6% w/w octylacrylamide acrylate copolymer and between 2% w/w and 3% w/w hydroxypropylcellulose. Octylacrylamide acrylate copolymer is commercially available, for example, under the tradename DERMACRYL, and hydroxypropylcellulose is available, for example, under the tradename KLUCEL.

The composition additionally contains a solvent. Suitable solvent can be an aqueous solvent, organic solvent, or mixture thereof. Organic solvents are those which are physiologically acceptable and compatible with the drug substance and the other ingredients of the composition including the film-forming polymer. Suitable solvents include ethanol, isopropanol, acetone and ethyl acetate. Preferred solvents are ethanol and a mixture of ethanol and water. The amount of water is in most cases less than the amount of the solvent. Typical water/solvent ratios are below 1:3. However in some cases the amount of water may exceed that of the solvent. It may then be up to 2.5:1. The solvent is used to solubilize or suspend the ingredients of the composition, and when the composition is applied on the skin, the solvent is evaporated and the composition forms an adhered film on the skin.

The composition of the invention may contain additional ingredients to improve the composition. Such ingredients include plasticizers, film modifiers, surfactants, penetration enhancers, coloring agents, antioxidants, complexing agents, and UV absorbers. Suitable plasticizers include dialkylphthalates, e.g. dibutylphthalate, hydroxy-fatty acid oils, e.g. castor oil, triglycerides and silicon oils. Film modifiers which change the properties of the film-forming polyer, in particular improve its application properties, e.g. hardness after evaporation of the solvent or flexibility on the skin. Suitable film modifiers include acrylic esters, arylsulfonamide-formaldehyde, cellulose derivatives or polyamides. Suitable surfactants, which help solubilization of the ingredients, include polyethylenglycol-alkylethers (e.g. as available under tradename BRIJ). Suitable penetration enhancers include azole, dimethylsulfoxide, unsaturated fatty alcohols, surfactants and propylene glycol.

The composition may additionally contain additional pharmaceutically active agents, including anti-inflammatory agents. Suitable anti-inflammatory agents include steroids, e.g., hydrocortisone, cortisone, dexamethasone, fluocinolone, triamcinolone, medrysone, prednisolone, flurandrenolide, prednisone, halcinonide, methylprednisolone, flurandrenolide, prednisone, halcinonide, methylprednisolone, fludrocortisone, corticosterone, paramethasone, and betamethasone; and non-steroidal anti-inflammatory drugs, e.g., ibuprofen, diclofenac, naproxen, fenoprofen, fenbufen, flurbiprofen, indoprofen, ketoprofen, suprofen, indomethacin, sulfasalazine, piroxicam, and aspirin. Of these particularly suitable are hydrocortisone, and diclofenac, indomethacin and salts thereof. The addition of the anti-inflammatory agent more quickly improves and cures the symptoms accompanying mycoses, such as itching, erythema, vesiculation, burning or fissures.

Another embodiment of the invention is characterized by pharmaceutical compositions comprising between 0.75% w/w and 20% w/w of terbinafine or a pharmaceutically salt thereof, between 0.05% w/w and 30% w/w of hydroxypropylcellulose, between 1% w/w and 10% w/w of octylacrylamide acrylate copolymer, and a solvent selected from the group consisting of ethanol, isopropanol, acetone and ethyl acetate. Especially preferred among those are pharmaceutical compositions, which in addition comprise a plasticizer selected from the group consisting of dialkylphthalates, hydroxy-fatty acid oils, triglycerides and silicon oils.

The composition is applied on the skin area infected by fungus to treat the infection. The composition is highly efficacious for treating fungal infections of the skin including tinea pedis, tinea corporis, tinea cruris, and tinea capitis. The composition is applied on the infected area of the skin and the solvent of the composition is allowed to evaporate. As the solvent evaporates, the composition forms a film on the skin, making an intimate contact with the skin to deliver the active agent directly to the area of infection. The composition has a mycological cure rate of at least 50% with a single-dose treatment, preferably at least 60%, more preferably at least 70%, and most preferably at least 80%. The mycological cure rate is determined by defining cure as negative microscopy and culture of the infected area of the skin six weeks after the treatment.

The composition of the invention is further illustrated with the following examples.

EXAMPLE 1

A liquid composition containing 1% terbinafine is prepared by combining 1.13% (w/w) of terbinafine hydrochloride salt, 5% octylacrylamide acrylate copolymer (Dermacryl 79), 5% medium chain triglyceride (Miglycol 812) and 2.5% hydroxypropylcellulose (Klucel MF), and 86.37% of 96% ethanol. A 5% terbinafine composition and a 10% terbinafine compositions are prepared by increasing the terbinafine content and decreasing the ethanol content proportionally. A placebo without the active agent is also prepared by proportionally increasing the other ingredients of the composition.

Patients with interdigital tinea pedis are enrolled and divided into four groups—107 patients for the 1% composition group, 99 patients for the 5% group, 93 patients for the 10% group, and 45 patients for the placebo group. Mycological species identified on the cultures of the patients include T. rubrum, T. mentagrophytes, and E. floccosum.

Each patient is treated once with one of the above four compositions by applying the composition to cover the four interdigital spaces, the sole, and the lateral surfaces up to approximately 1.5 cm. 6 weeks after the treatment, the infected skin areas of the patients are examined by direct microscopy, culture and clinical signs and symptoms. The symptoms including erythema, desquamation, pruritus, pustules, vesiculation, and incrustation are scored by the investigator using a 4-point scale. The efficacy endpoint is the rate of effective treatment at week 6, defined as negative microscopy and culture. Mycological cure is defined as negative microscopy and culture.

The mycological cure rates at week 6 are very high in all three groups treated with the terbinafine compositions and significantly higher than the rate in the placebo group, as can be seen from Table 1.

TABLE 1

| | Success rate (%) Composition | | | |
|---|---|---|---|---|
| | 1% | 5% | 10% | Placebo |
| Negative culture | 91 | 88 | 97 | 33 |
| Negative microscopy | 87 | 83 | 83 | 42 |
| Mycological cure | 84 | 80 | 83 | 27 |

The success rate result indicated in Table 1 demonstrates the high cure efficacy of the present composition, even with the composition containing a low concentration of the antifungal active. The mycological cure rate for the compositions ranges from 80% to 83% with only one application. The cure rate of the present compositions is similar to the cure rate obtained by currently available commercial over-the-counter antifungal products when these products are administered in strict adherence to the required regimen of one or two daily applications for one to four weeks. The ease of administration and dosing of the present composition encourages infected individuals to undertake the treatment, encouraging high compliance outcomes and reducing spread of infection.

EXAMPLE 2

A 1% terbinafine liquid composition is prepared in accordance with Example 1. Patients with interdigital tinea pedis are treated with the liquid composition once and check for the effectiveness of the treatment at week 6. Effective treatment is defined as negative mycological presence and minimal signs of symptoms (i.e., erythema, desquamation, pruritus, pustules, vesiculation, and incrustation). The patients who are effectively treated are again checked for culture at week 12 for a re-infection evaluation.

Only one in eight of the treated patients has a positive culture at week 12, indicating re-infection. This result is similar to the rate of re-infection observed in a study with a commercial 1% terbinafine cream product, Lamisil® cream, applied twice daily for seven days. The Lamisil product is used as a comparison product since the product has the simplest treatment regimen requirement among the antifungal product currently available in the over-the-counter market, i.e., once daily for only seven days. The result demonstrates that the present film-forming composition, which only requires one treatment application, is an effective and convenient treatment for fungal infections of the skin.

EXAMPLE 3

A 5% terbinafine liquid composition is prepared in accordance with Example 1. The composition is applied to form adhered film areas on the backs of patients, delivering a single dose of 250 µg per cm$^2$ of terbinafine per treatment area. The patients are divided into three groups. For one group the applied film is removed by gently washing with a sponge impregnated with soapy water at 2 hours from the application. For another group, the applied film is removed at 12 hours from the application. The stratum cornea of the patents is investigated for absorption pharmacokinetics. The pharmacokinetics study indicates that about 30% of terbinafine reaches the stratum cornea in the first two hours, about 31% in the following two to twelve hours, and about 39% after twelve hours. Additionally, the $C_{max}$ is observed as soon as one hour among the treated patients.

EXAMPLE 4

A 1% terbinafine liquid composition is prepared in accordance with Example 1. The composition is applied to form adhered film areas on the backs of one group of patients, delivering a single dose of 50 µg per cm$^2$ per treatment area. To another group of patients, a commercial 1% terbinafine cream product, Lamisil® cream, is applied in the same manner and concentration as the film composition, except that the cream is applied daily for seven days. The treated stratum cornea of both groups of the patients are tested for the terbinafine concentration in 13 days from the initial treatment. Pharmacokinetic analyses indicate that the mean terbinafine concentrations of terbinafine of the two groups are at a similar level, indicating that one application of the film composition is as efficacious as the cream treatment applied for seven days. The present composition is a highly efficacious composition for treating fungal infections of the skin. It typically requires only one application to treat the fungal infection, making it highly convenient and easy for patients to comply with the treatment regimen to a successful cure of the infection.

What is claimed is:

1. A one dose method of treatment of a dermatophyte skin infection selected from tinea pedis, tinea corporis, tinea cruris and tinea capitis, said method comprising topically applying to the infected skin a single dose of a film-forming composition capable of adhering to the skin for a period of at least 48 hours, and maintaining said composition on the skin for at least 48 hours, said composition comprising upon application
    a) an antifungal agent terbinafine or a salt thereof,
    b) a hydrophilic film-forming agent comprising a hydroxyalkyl cellulose, and
    c) a hydrophobic film-forming polymer selected from the group consisting of octylacrylamide, octylacylamide acrylate copolymer; octylpropenamide acrylate copolymer, in a solvent selected from an aqueous solvent, organic solvent, or a mixture thereof,
    whereby said single dose application of said composition results in sufficient absorption of the antifungal agent by the stratum corneum to provide effective treatment of the dermatophyte skin infection, said effective treatment consisting of a mycological cure rate of at least 50% at six weeks following application of said single dose.

2. The method of claim 1 wherein said hydrophobic film-forming polymer is octylacrylamide acrylate copolymer.

3. The method of claim 1 wherein said composition comprises between 0.75% w/w and 20% w/w of terbinafine or a salt thereof, 0.05% w/w and 30% w/w of a mixture of octylacrylamide acrylate copolymer and hydroxypropylcellulose, and a solvent selected from the group consisting of ethanol, isopropanol, acetone and ethyl acetate.

4. The method of claim 1 wherein said hydrophobic film-forming polymer is octylacrylamide acrylate copolymer present in an amount of about 3 to about 7% w/w.

5. The method of claim 1 wherein said composition comprises between 0.75% w/w and 20% w/w of terbinafine or a salt thereof, between 0.05% w/w and 30% w/w of a mixture of octylacrylamide acrylate copolymer and hydroxypropylcellulose, and a solvent selected from the group consisting of ethanol and a mixture of ethanol and water.

6. The method of claim 5 wherein the solvent is a mixture of ethanol and water and the ratio of water to solvent is below 1:3.

7. The method of claim 1 wherein the plasticizer comprises a medium chain triglyceride.

8. The method of claim 1 comprising 1% terbinafine or salt thereof.

9. The method of claim 1 wherein the hydrophilic film-forming agent is hydroxypropylcellulose.

10. The method of claim 3 wherein the solvent further comprises water.

11. A method of treating skin infected with dermatophytes in a human in need thereof, the method comprising topically applying to the infected skin a one-time dose of a film-forming composition capable of adhering to the skin for a period of at least 48 hours, maintaining said composition on the skin for at least 48 hours, said composition comprising upon application
  a) an antifungal agent terbinafine or a salt thereof,
  b) a hydrophilic film-forming agent comprising a hydroxyalkyl cellulose, and
  c) a hydrophobic film-forming polymer selected from the group consisting of octylacrylamide, octylacylamide acrylate copolymer; octylpropenamide acrylate copolymer, in a solvent selected from an aqueous solvent, organic solvent, or a mixture thereof,
  whereby said single dose application of said composition provides an effective treatment of the dermatophyte skin infection, said effective treatment consisting of a mycological cure rate of at least 50% at six weeks following application of said single dose wherein the composition additionally comprises a plasticizer selected from the group consisting of dialkylphthalates, hydroxyl-fatty acid oils, triglycerides and silicon oils.

12. The method according to claim 11 wherein the terbinafine or a salt thereof, is present in an amount of about 1 to about 10% w/w.

13. The method according to claim 12 comprising 10% terbinafine or salt thereof.

14. The method according to claim 12 comprising 5% terbinafine or salt thereof.

15. The method according to claim 12 comprising 1% terbinafine or salt thereof.

16. The method according to claim 11 wherein the hydrophilic film-forming agent is present in an amount of about 1 to about 10% w/w.

17. The method according to claim 11 wherein the hydrophobic polymer is present in an amount of about 1 to about 7% w/w.

18. The method according to claim 11 wherein the solvent is selected from ethanol isopropanol, acetone and ethyl acetate.

19. The method according to claim 18 wherein the solvent is a mixture of water and a solvent.

20. The method according to claim 19 wherein the water to solvent is in a ratio of below 1:3.

21. The method according to claim 19 wherein the solvent is ethanol.

22. The method according to claim 20 wherein the solvent is ethanol.

23. The method according to claim 11 wherein the plasticizer is a medium chain triglyceride.

24. The method according to claim 11 wherein the dermatophyte skin infection is tinea pedis, tinea corporis, tinea crusis or tinea captitis.

* * * * *